(12) United States Patent
Aghassian

(10) Patent No.: US 8,755,900 B2
(45) Date of Patent: *Jun. 17, 2014

(54) PRESSURE-SENSITIVE EXTERNAL CHARGER FOR AN IMPLANTABLE MEDICAL DEVICE

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/057,615

(22) Filed: Oct. 18, 2013

(65) Prior Publication Data

US 2014/0046405 A1    Feb. 13, 2014

Related U.S. Application Data

(60) Division of application No. 13/768,911, filed on Feb. 15, 2013, now Pat. No. 8,644,949, which is a continuation of application No. 12/689,392, filed on Jan. 19, 2010, now Pat. No. 8,401,663.

(51) Int. Cl.
*A61N 1/378* (2006.01)

(52) U.S. Cl.
USPC ............... 607/61; 607/60; 607/32; 607/33

(58) Field of Classification Search
USPC ........................................ 607/32–33, 60–61
See application file for complete search history.

(56) References Cited

U.S. PATENT DOCUMENTS

| | | | |
|---|---|---|---|
| 6,516,227 B1 | 2/2003 | Meadows et al. | |
| 7,650,192 B2 | 1/2010 | Wahlstrand | |
| 8,214,042 B2 | 7/2012 | Ozawa et al. | |
| 8,244,367 B2 | 8/2012 | Wahlstrand et al. | |
| 8,321,029 B2 | 11/2012 | Aghassian | |
| 8,335,569 B2 | 12/2012 | Aghassian | |
| 8,401,663 B2 * | 3/2013 | Aghassian | ..................... 607/61 |
| 2008/0027500 A1 | 1/2008 | Chen | |
| 2009/0118796 A1 | 5/2009 | Chen et al. | |
| 2011/0087307 A1 | 4/2011 | Carbunaru et al. | |

* cited by examiner

*Primary Examiner* — Joseph Stoklosa
(74) *Attorney, Agent, or Firm* — Wong, Cabello, Lutsch, Rutherford & Brucculeri, LLP.

(57) ABSTRACT

An improved external charger for an implantable medical device is disclosed in which charging is at least partially controlled based on a sensed pressure impingent on its case, which pressure is indicative of the pressure between the external charger and a patient's tissue. The improved external charger includes pressure detection circuitry coupled to one or more pressure sensors for controlling the external device in accordance with the sensed impingent pressure. The sensed pressure can be used to control charging, for example, by suspending charging, by adjusting a maximum set point temperature for the external charger based on the measured pressure, or by issuing an alert via a suitable user interface. By so controlling the external charger on the basis of the measured pressure, the external charger is less likely to create potentially problematic or uncomfortable conditions for the user.

18 Claims, 13 Drawing Sheets

PRESSURE-SENSITIVE EXTERNAL CHARGER FOR AN IMPLANTABLE MEDICAL DEVICE

CROSS REFERENCE TO RELATED APPLICATIONS

This is a divisional of U.S. patent application Ser. No. 13/768,911, filed Feb. 15, 2013 (now allowed), which is a continuation of U.S. patent application Ser. No. 12/689,392, filed Jan. 19, 2010 (now U.S. Pat. No. 8,401,663). Priority is claimed to both of these applications, and both are incorporated herein by reference in its entireties.

FIELD OF THE INVENTION

The present invention relates generally to implantable medical device systems, and more particularly to an external device such as an external charger for an implantable medical device controllable on the basis of pressure impingent upon its case.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a Spinal Cord Stimulation (SCS) system, such as that disclosed in U.S. Pat. No. 6,516,227 ("the '227 patent"), which is incorporated herein by reference in its entirety.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium, for example. The case 30 usually holds the circuitry and power source or battery necessary for the IPG to function. The IPG 100 is coupled to electrodes 106 via one or more electrode leads (two such leads 102a and 102b are shown), such that the electrodes 106 form an electrode array 110. The electrodes 106 are carried on a flexible body 108, which also houses the individual signal wires 112a-112p, coupled to each electrode. The signal wires 112 a-112p are connected to the IPG 100 by way of an interface 115, which may be any suitable device that allows the leads 102 (or a lead extension, not shown) to be removably connected to the IPG 100. Interface 115 may comprise, for example, an electro-mechanical connector arrangement including lead connectors 38a and 38b configured to mate with corresponding connectors on the leads. In the illustrated embodiment, there are eight electrodes on lead 102a, labeled $E_1$-$E_8$, and eight electrodes on lead 102b, labeled $E_9$-$E_{16}$, although the number of leads and electrodes is application specific and therefore can vary. The electrode array 110 is typically implanted along the dura of the spinal cord, and the IPG 100 generates electrical pulses that are delivered through the electrodes 106 to the nerve fibers within the spinal column. The IPG 100 itself is then typically implanted somewhat distantly in the buttocks of the patient.

As shown in FIG. 2, an IPG 100 typically includes an electronic substrate assembly 14 including a printed circuit board (PCB) 16, along with various electronic components 20, such as microprocessors, integrated circuits, and capacitors, mounted to the PCB 16. Ultimately, the electronic circuitry performs a therapeutic function, such as neurostimulation. A feedthrough assembly 24 routes the various electrode signals from the electronic substrate assembly 14 to the lead connectors 38a, 38b, which are in turn coupled to the leads 102 (see FIGS. 1A and 1B). The IPG 100 further comprises a header connector 36, which, among other things, houses the lead connectors 38a, 38b. The IPG 100 can further include a telemetry antenna or coil (not shown) for receipt and transmission of data to an external device such as a portable or hand-held or clinician programmer (not shown), which can be mounted within the header connector 36. As noted earlier, the IPG 100 usually also includes a power source, and in particular a rechargeable battery 26.

Also shown in FIG. 2 is an external charger 12 that is used to recharge the battery 26 in the IPG 100, which is explained in further detail below. The external charger 12 itself needs power to operate, and therefore may include its own battery 70, which may also be a battery that is rechargeable using a plug-in-the-wall holster ("cradle") or power cord connection much like a cellular telephone. Alternatively, the external charger 12 may lack a battery and instead draw its power directly from being plugged into a wall outlet (not shown).

The external charger 12 can contain one or more printed circuit boards 72, 74, which contain the circuitry 76 needed to implement its functionality. In one embodiment, and as shown in FIG. 2, most of the circuitry 76 can be located on an orthogonal circuit board 74, which reduces interference and heating that might be produced by the charging coil 17 positioned on circuit board 72, as is further explained in U.S. patent application Ser. No. 11/460,955, filed Jul. 28, 2006. The external charger 12 also consists of a case or housing 15, typically formed of a hard plastic, which may be divided into top and bottom portions 15a and 15b. The case 15 can be hand-held, or body-worn, or portable. Junction 13 illustrates the location where the top and bottom portions 15a and 15b may be snapped together or connected by other means. Clamps 19 may be utilized to hold the circuit boards 72 and 74 in place mechanically. Clamps 19 are shown formed as a part of the bottom case portion 15b, although this is not strictly necessary, as other means can be used to stabilize the components within the case 15.

To wirelessly transmit energy 29 between the external charger 12 and the IPG 100, and as shown in FIG. 2, the charger 12 typically includes an alternating current (AC) coil 17 that supplies energy 29 to a similar charging coil 18 located in or on the IPG 100 via inductive coupling. In this regard, the coil 17 within the external charger 12 is wrapped in a plane which lies substantially parallel to the plane of the coil 18 within the IPG 100. Such a means of inductive energy transfer can occur transcutaneously, i.e., through the patient's tissue 25. The energy 29 received by the IPG's coil 18 can be rectified and used to recharge battery 26 in the IPG 100, which in turn powers the electronic circuitry that runs the IPG 100. Alternatively, the energy 29 received can be used to directly power the IPG's electronic circuitry, which may lack a battery altogether.

Inductive charging between the two coils 17 and 18 can produce significant heating in the external charger 12. Because the external charger 12 is in proximity with the patient's tissue 25, there is the risk that high temperatures in the external charger 12 could overheat (or burn) the skin of the patient. Accordingly, techniques have been proposed for controlling external chargers to ensure that safe temperatures are not exceeded. Usually, such techniques involve monitoring the temperature of the external charger by a thermocouple or thermistors. Should a threshold temperature be exceeded (Tmax), generation of the magnetic charging field at the external charger is temporarily suspended to allow the external charger time to cool. At some later point, perhaps once the temperature falls a few degrees below Tmax (i.e., to Tmin), charging can once again be enabled, with the process essentially duty cycling the charging coil 17 in external charger on and off, as shown in FIG. 3.

Despite such solutions, the inventor considers that further improvements can be made to the safety of external charger technology, and this disclosure provides one such solution, in which an external charger is controlled based on a pressure impingent on its case.

DETAILED DESCRIPTION

The inventor has realized that heat transfer between an external charger and a patient's tissue is increased as the pressure between the two is increased. As a result, an external charger at a given temperature will transfer more heat—and thus will feel hotter—to a patient as the pressure is increased. This is significant when one realizes that an external charger is often held or pressed firmly against the patient's skin. For example, an external charger for an IPG is often placed in a retaining belt or "fanny pack," or integrated in other structures such as mattress pads, that the patient may lean against or lie upon, and which would tend to press the external charger against the patient.

To address these realities, an improved external charger for an implantable medical device is disclosed in which charging is at least partially controlled based on a sensed pressure impingent on its case, which pressure is indicative of the pressure between the external charger and a patient's tissue. The improved external charger includes pressure detection circuitry coupled to one or more pressure sensors for controlling the external device in accordance with the sensed impingent pressure. The sensed pressure can be used to control charging, for example, by suspending charging, by adjusting a maximum set point temperature for the external charger based on the measured pressure, or by issuing an alert via a suitable user interface. By so controlling the external charger on the basis of the measured pressure, the external charger is less likely to create potentially problematic or uncomfortable conditions for the user.

Figures 1A, 1B:
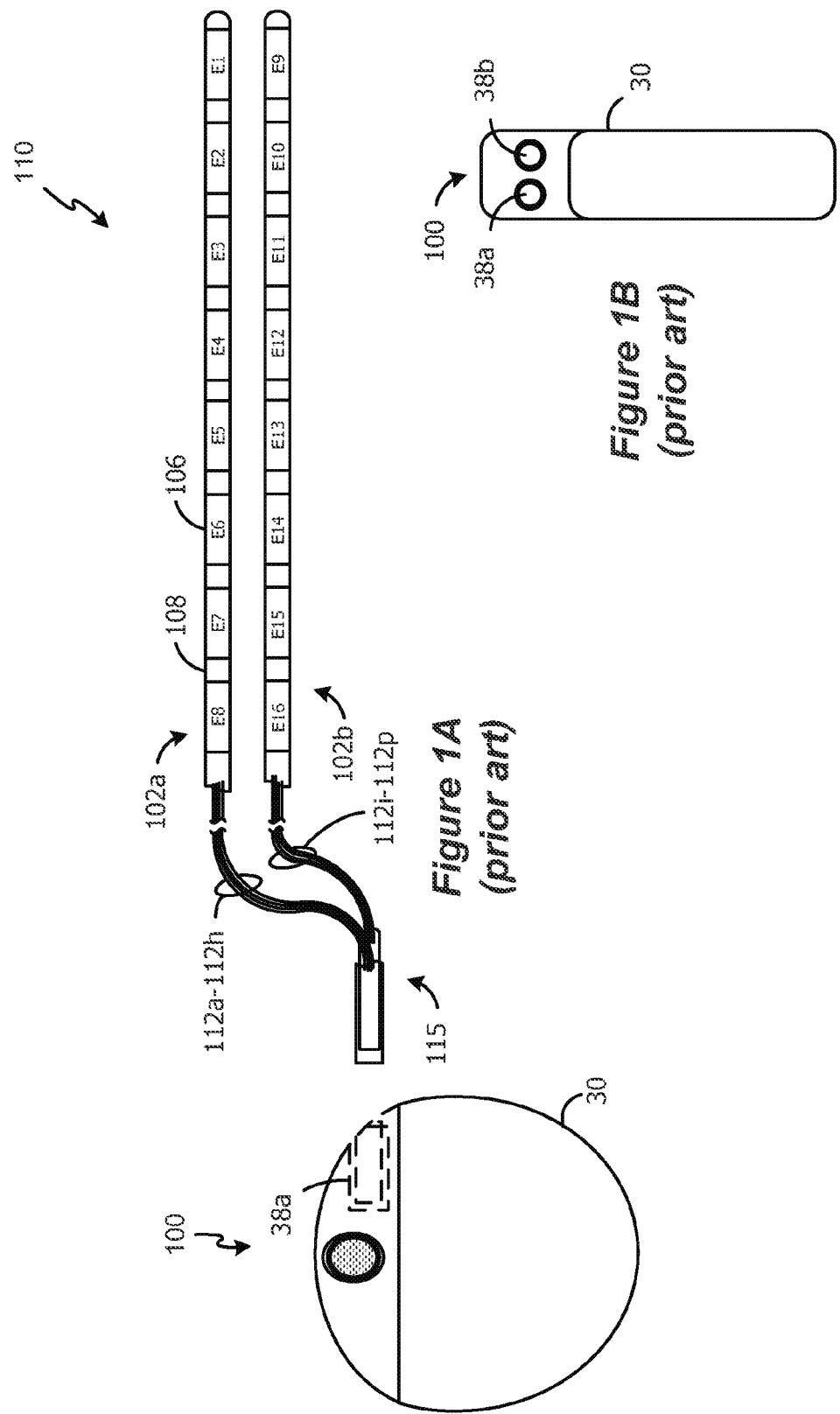
FIGS. 1A and 1B show an implantable pulse generator (IPG), and the manner in which an electrode array is coupled to the IPG, in accordance with the prior art.
Figure 2:
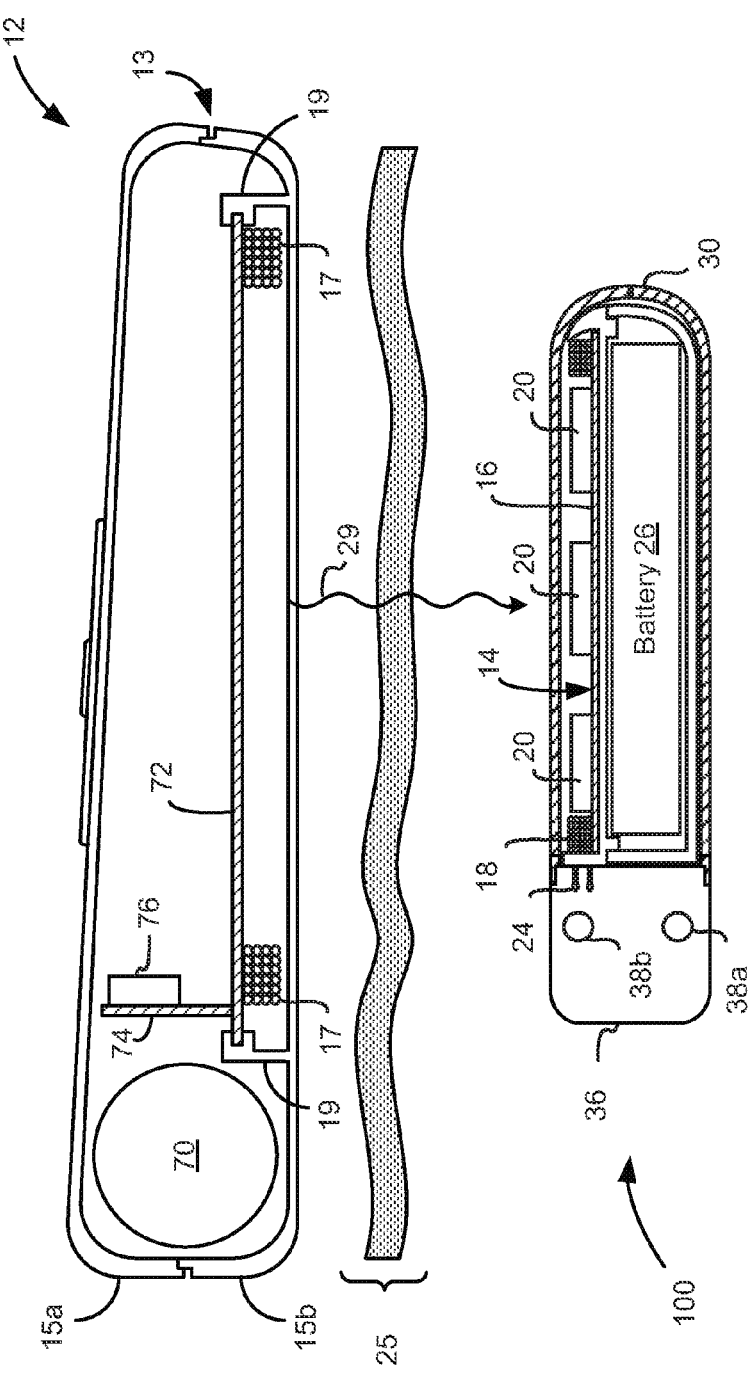
FIG. 2 shows the IPG in relation to an external charger, in accordance with the prior art.
Figure 4:
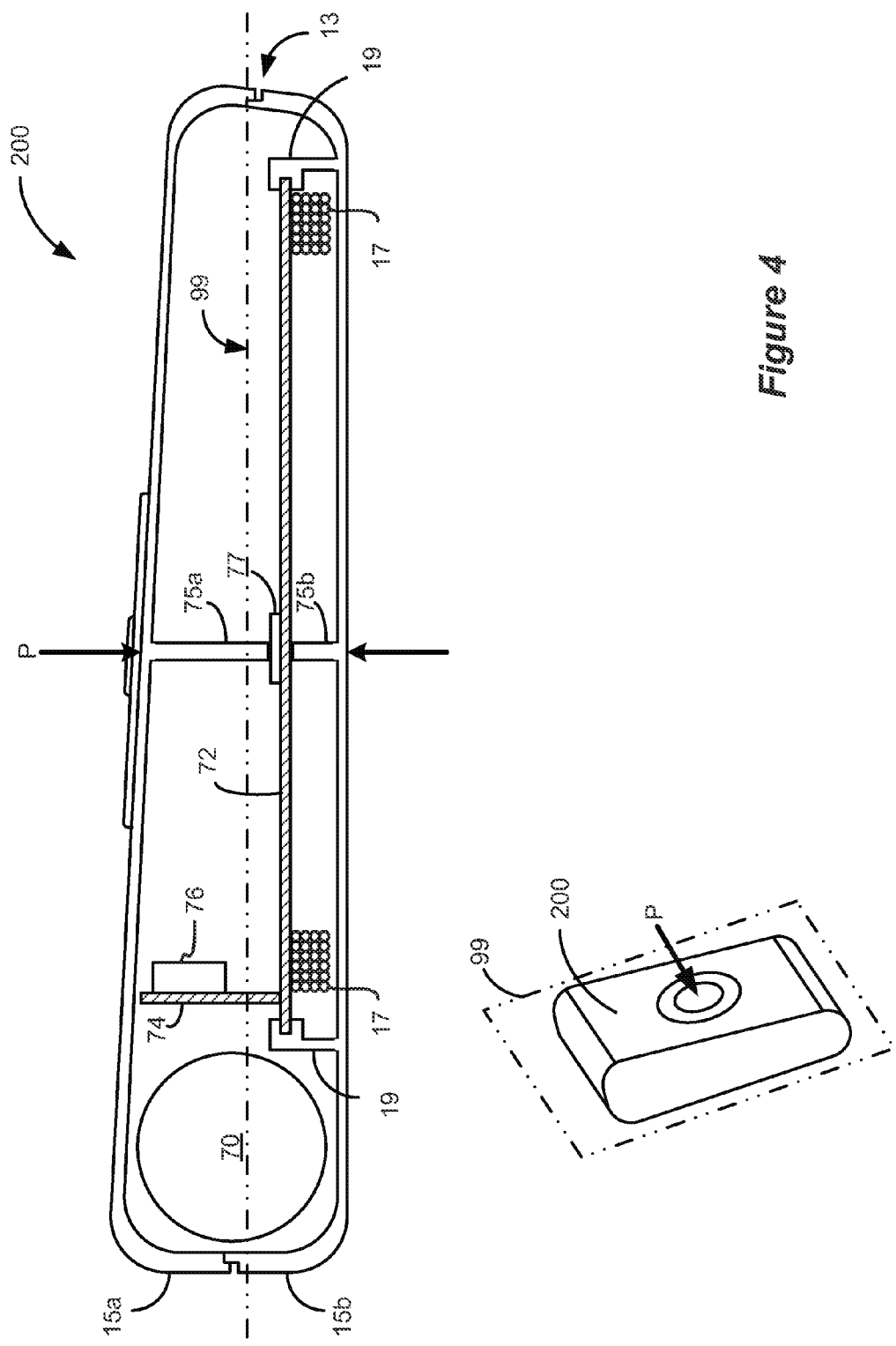
FIG. 4 shows an embodiment of an improved external charger, which includes a pressure sensor and associated pressure detection circuitry.

FIG. 4 shows an embodiment of the improved external charger 200. Many of the components in improved external charger 200 are the same as those appearing in the prior art charger 12 of FIG. 2, and, for simplicity, such components are not described again in detail. Newly-added to the external charger 200 is a pressure sensor 77 and transfer elements 75a and 75b for transmitting an externally-applied pressure P to the pressure sensor 77. Pressure P represents a pressure impingent on the case 15 of the external charger 200, which pressure can result from forcing the external charger 200 toward the patient's tissue. For example, pressure P can result from tight clothing or a tight retaining belt, from squeezing the external charger 200 between the patient and a piece of furniture in which the patient is residing, etc. The pressure sensor 77 may comprise, for example, part number IESF-R-5, manufactured by CUI, Inc.

As shown in FIG. 4, the external charger 200 has a case 15 that is substantially planar in design as is typical, meaning that case 15 can be confined to a plane 99 parallel with one of its major surfaces. Such substantially planar shape for the case 15 facilitates placing the external charger 200 against the skin of a patient as already mentioned. The sensed impingent pressure, P, is orthogonal to plane 99 of the external charger 200, which is sensible because the planar design of the case will create a large force vector in this orthogonal direction when pressed against the patient.

Transfer elements 75a and 75b may comprise cylindrical posts or other mechanical members respectively affixed to the top and bottom case portions 15a and 15b. In the example shown, the elements 75 are formed as part of (e.g., molded with) the case portions 15a and 15b, but this is not strictly necessary. As also shown, pressure sensor 77 is affixed to one side of the PCB 72, which location is convenient, as pressure sensor 77 comprises a portion of pressure detection circuitry 250 (FIG. 5A) residing on the PCB 72 (or orthogonal PCB 74). However, the pressure sensor 77 could also intervene between one of the elements 75a or 75b and its corresponding case portion. If a given external charger has a very thin case 15, transfer elements 75a or 75b may not be required at all, or only one transfer element may be needed. Although not shown in FIG. 4, a pressure sensor 77 could also be located in the notched area 13 between the top and bottom halves of the external charger's case 15a and 15b, which would obviate the need for transfer elements 75a and 75b altogether. Furthermore, more than one pressure sensor 77 can be used to assess the pressures at a plurality of locations within the case 15, perhaps with an average of the determined pressures being used to control the external charger 200. In short, any means of transferring pressure P to one or more pressure sensors 77 will suffice, thus allowing flexibility in positioning the pressure sensor(s) 77 within a given case 15.

Figure 5A:
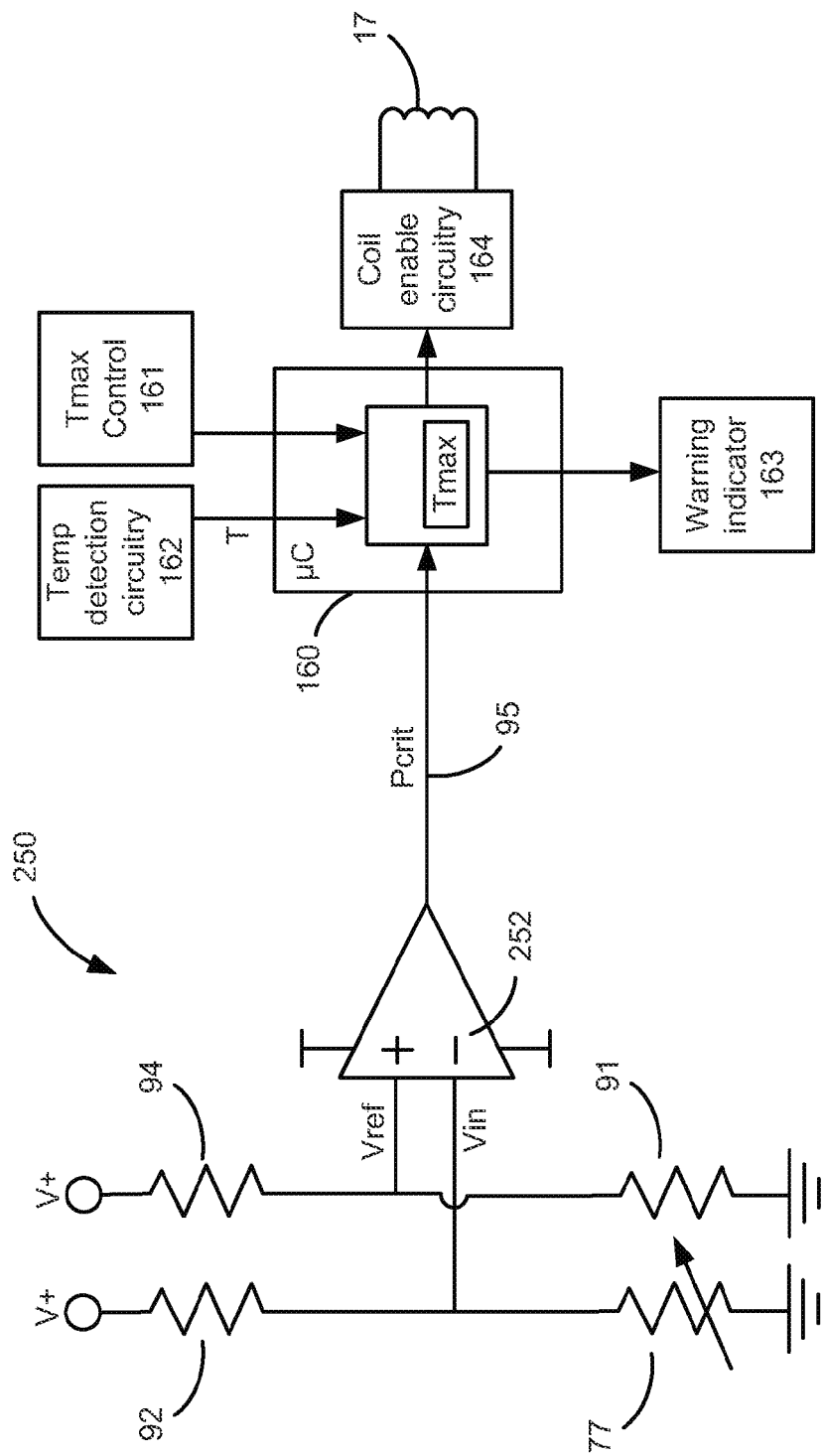
FIGS. 5A and 5B show control of the temperature of the external charger of FIG. 4 as a function of a critical sensed pressure.

FIG. 5A shows an example of pressure detection circuitry 250 useable in the external charger 200 for detecting when the pressure on the case is above or below a critical pressure, Pcrit, at which control for the external charger 200 will be changed. In the example shown, the pressure sensor 77 comprises a variable resistor, which can vary in resistance >500 kΩ at no load (i.e., P=0) to <500Ω at a full load, to cite representative values. Pressure sensor 77 forms a voltage divider with resistor 92 to provide an input, Vin, to a comparator 252 which, in this example, produces a digital output, Pcrit. The other input to the comparator 252 comprises a reference voltage, Vref, set by a voltage divider formed by two fixed resistors 94 and 91. By appropriately setting the values for resistors 91, 92, and 94 in relation to the resistance of the pressure sensor 77, Vin can be made smaller than Vref at pressures above Pcrit, and can be made larger than Vref at pressures below Pcrit, resulting in a digital output from the comparator 95 of Pcrit='1' or '0', respectively. In short, the values of the resistances can be used to set Pcrit.

Pcrit is preferably set by the manufacturer such that a pressure value slightly below Pcrit should not discomfort a heat-sensitive patient even if applied for a relatively long duration, such as 30 minutes. However, because pain thresholds and tolerance levels vary from patient to patient, Pcrit may be programmable after manufacture to allow a user or clinician to adjust Pcrit if necessary. Such programming can modify the resistances of resistors 91, 92, or 94 for example, and can be accomplished via a user interface of the external charger 200 (not shown).

As shown in FIG. 5A, the Pcrit digital output signal 95 is sent to the microcontroller 160 in the external charger 200, which may comprise part of circuitry 76 (see FIG. 4). As discussed in further detail below, Pcrit can be used by the microcontroller 160 to, e.g., (1) adjust thermal control of the external charger 200, such as by adjusting Tmax, (2) suspend charging altogether by disabling the external charger 200's coil, or (3) issue an alert to the patient about the unsafe pressure. In certain embodiments, microcontroller 160 will also record Pcrit as a function of time, which can allow for more sophisticated external charger 200 control. For example, if a high pressure, e.g., Pcrit='1', is merely transitory (e.g., less than a second or so), or sporadic (e.g., occurring only a few times a minute), it may be unnecessary to take any of actions (1), (2), or (3) above. However, in many of the examples provided below, it is assumed for simplicity that action is taken immediately upon the assertion of Pcrit='1'.

Figure 3:
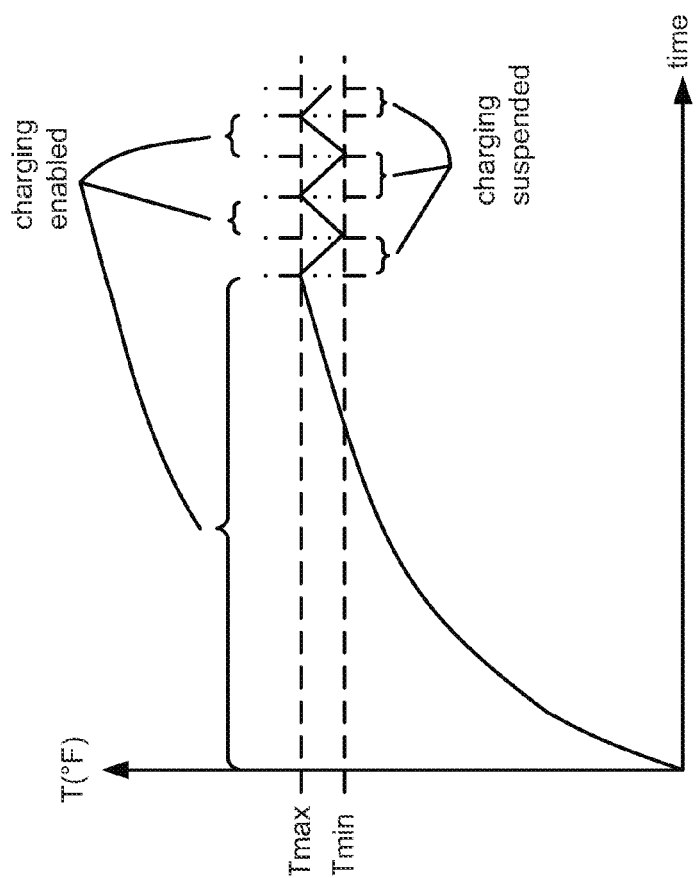
FIG. 3 shows regulation of the external charger's temperature during IPG battery charging, in accordance with the prior art.
Figure 5B:
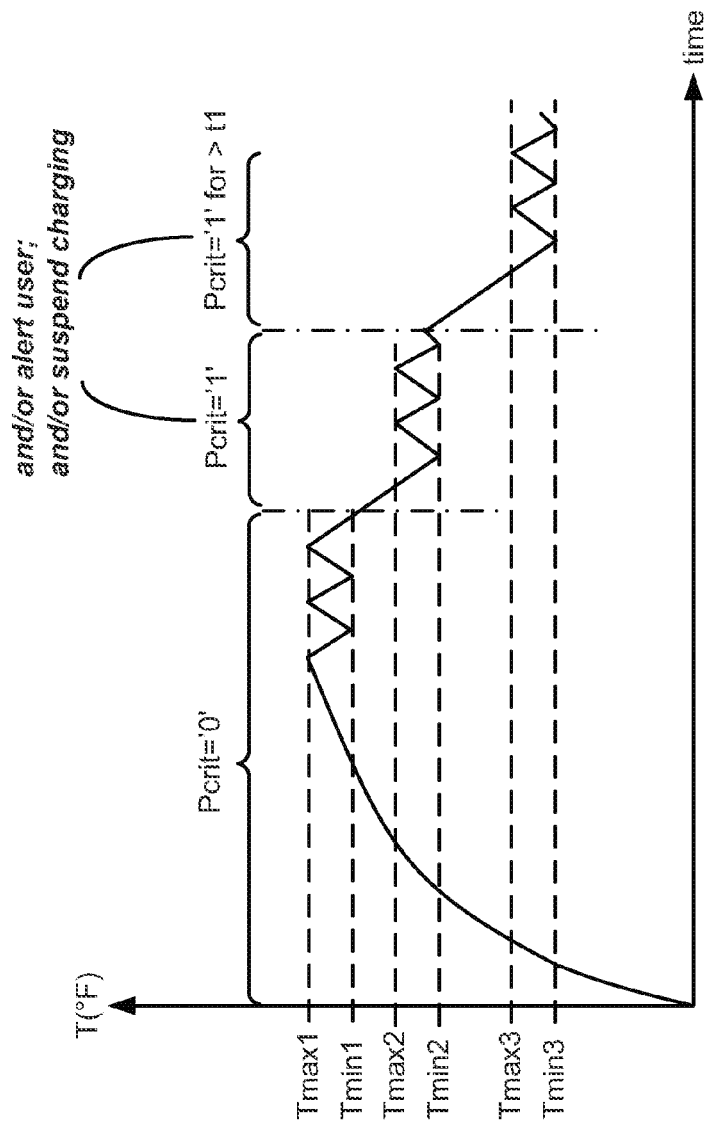

FIG. 5B shows, in graphical form, how Pcrit is used to control the external charger 200 by adjusting Tmax, i.e., the maximum set-point temperature of the external charger 200, as discussed earlier with reference to FIG. 3. In FIG. 5B, the external charger 200 begins charging with an initial maximum temperature set point of Tmax1. Tmax1 may be programmed by the manufacturer, or may be set by the user in conjunction with Tmax control circuitry 161 (FIG. 5A). Setting or changing of a Tmax value for an external charger is discussed in U.S. patent application Ser. No. 12/562,694, filed Sep. 18, 2009 ("the '694 application"), which is incorporated herein by reference in its entirety, and which discloses circuitry suitable for Tmax control 161. FIG. 5B assumes that, initially, the pressure impingent upon the external charger 200 is low (Pcrit='0'), meaning that Tmax1 comprises an appropriate maximum temperature for the external charger. Temperature control in the external charger is established during such non-critical pressure conditions in accordance with the prior art, i.e., the temperature T of the external charger is monitored by temperature detection circuit 162 and reported to the microcontroller 160; when Tmax1 is exceeded, charging is temporarily suspended and microcontroller 160 disables coil enable circuitry 164 to shut off charging coil 17; at some time later after the sensed temperature has dropped (e.g., to Tmin1), charging is again enabled, etc.

However, when pressure detection circuitry 250 reports an increase in pressure, e.g., to Pcrit='1', microcontroller 160 establishes a new, lower maximum temperature Tmax2. This is done in recognition that the higher pressure will allow for more heat transfer from the external charger 200 to the patient, and accordingly that the old, higher maximum temperature set point Tmax1 may no longer by tolerated by the patient. Adjusting Tmax to Tmax2 may occur as disclosed in the above-incorporated '694 application.

With Tmax dropped to Tmax2, and as shown in FIG. 5B, the temperature of the external charger 200 falls to lower, safer temperatures. Although not illustrated in FIG. 5B, should the pressure P fall and Pcrit='0' once again, then microcontroller 160 can restore the maximum temperature back to Tmax1. However, microcontroller 160 may require that Pcrit='0' for some predetermined amount of time (e.g., some number of minutes) before resetting Tmax from Tmax2 to Tmax1.

Upon assertion of the high-pressure condition, Pcrit='1', the microcontroller 160 may alter the user of the external charger 200 of the potentially unsafe pressure condition via warning indicator 163 (FIG. 5A), or may simply suspend further charging by disabling coil enable circuitry 164 (FIG. 5A). Such options are not mutually exclusive. For example, the microcontroller 160 may: alert the user and continue charging at the higher maximum temperature Tmax1; alert the user and continue charging at the lower maximum temperature Tmax2; alert the user and suspend charging, or simply suspend charging. The alert issued by warning indicator 163 could be issued via any suitable user interface on the external charger or otherwise, and can comprise any sort of visual (e.g., blinking lights, display of graphics or text on a graphical user interface), auditory (beeps, synthesized speech), or tactile (e.g., vibration) feedback suitable for interpretation by the user of the external charger 200.

Should high-pressure condition Pcrit='1' exist for a critically long period of time, t1, then microcontroller 160 may lower the maximum temperature to an even lower temperature, Tmax3, as shown in FIG. 5B. Dropping the maximum temperature once again to Tmax3 recognizes that, after the critical time period, the patient's compressed tissue may have taken up substantial amounts of heat and can no longer continue to do so at such a high rate. Alternatively, and as discussed above, the microcontroller 160 may, at this point, alert the patient or suspend charging in accordance with any of the combinations discussed above.

To this point, temperature control upon detection of a critical pressure is achieved by lowering the maximum temperate, Tmax, through a duty cycling scheme, such as that disclosed in the above-incorporated '694 application. However, it should be realized that useful applications of the invention are not so limited, and instead detection of a critical pressure can be used to modify other temperature control schemes for an external charger. For example, instead of duty cycling the charging coil 17 in accordance with a lower set point temperature when Pcrit='1', the current through coil 17 can be lowered to prevent overheating. Or, a particular program operable in the external charger 200 for stimulating the coil 17 in a particular way can be modified upon the detection of a high pressure so as to reduce the temperature. In short, the disclosed techniques can be used to control the temperature of the external charger on the basis of detected pressure through any means.

Figure 6A:
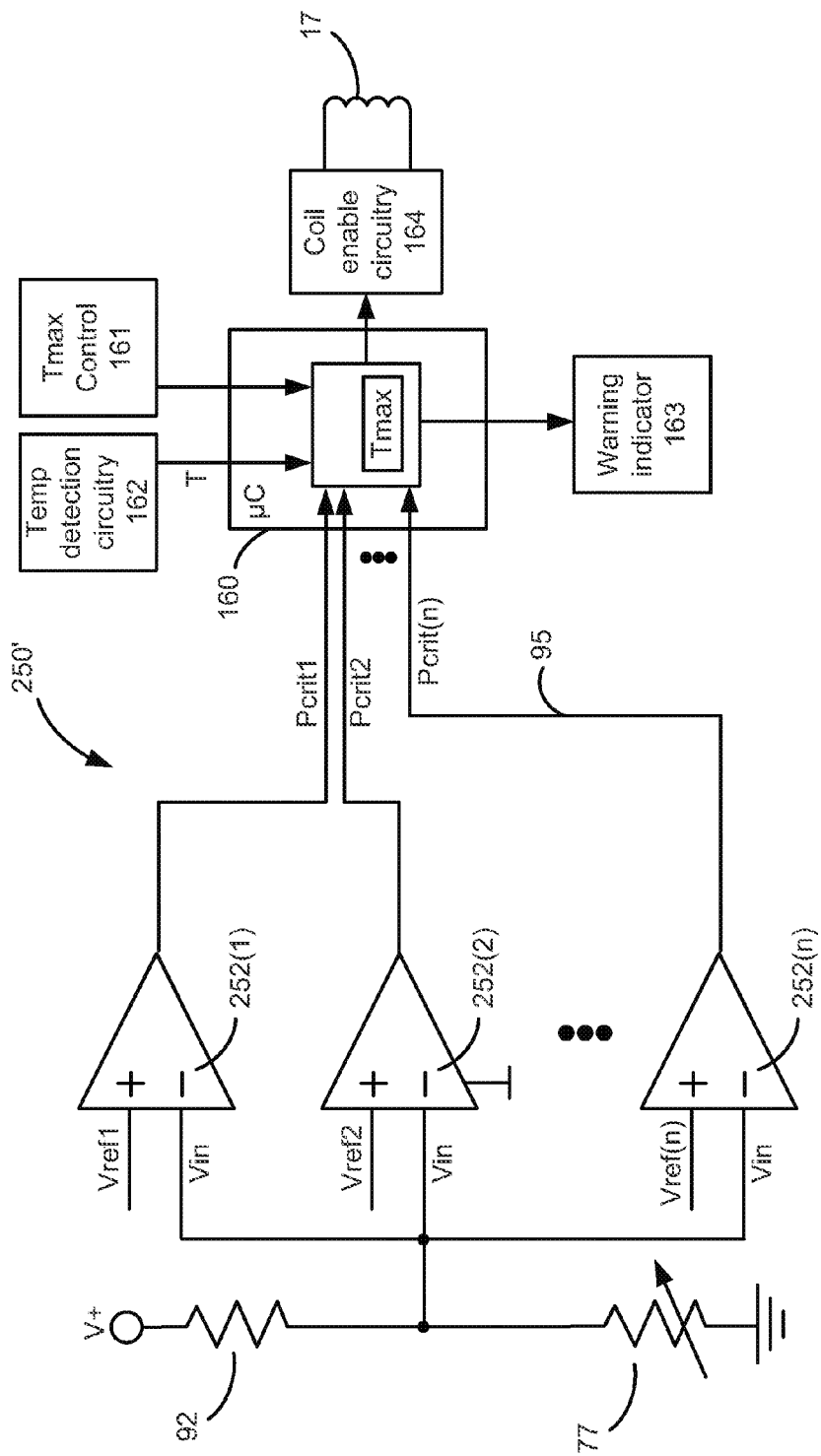
FIGS. 6A and 6B show control of the temperature of the external charger of FIG. 4 as a function of a plurality of sensed pressure ranges.
Figure 6B:
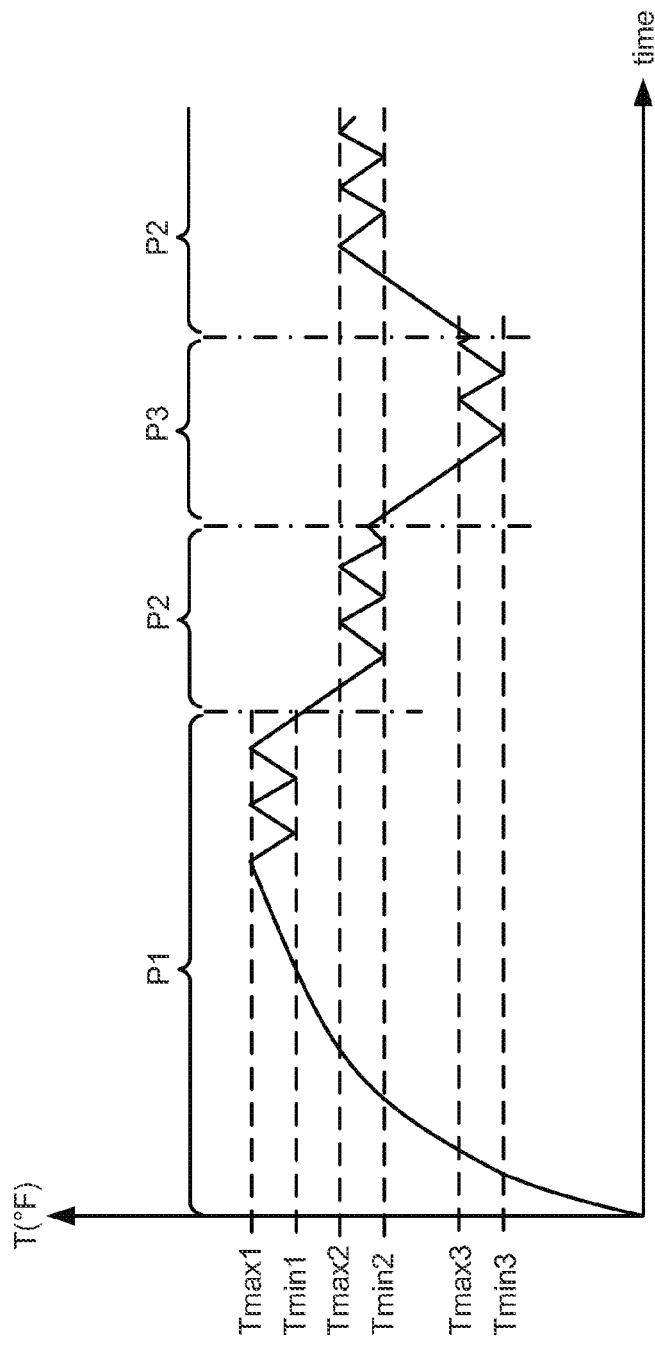

To this point, control of the external charger 200 has occurred on the basis of a single value, Pcrit, indicative of a critical pressure on the external charger's case 15. However, control need not be so limited to a single critical pressure. FIGS. 6A and 6B illustrate control of external charger temperature using several discrete pressure ranges, P(x), with each range being assigned a different maximum temperature set point, Tmax(x). This allows the maximum temperature to be set as a function of the pressure, with increasing pressures causing decreasing maximum set-point temperatures. Thus, as the impingent pressure increases (from P1 to P2 to P3), the maximum temperature for the external charger 200 decreases (from Tmax1 to Tmax2 to Tmax3), as shown in FIG. 6B. In other words, the pressure detection circuitry controls the external charger by scaling a maximum set-point temperature for the external charger inversely with the impingent pressure.

Allowing for control of the external device in accordance with a plurality of discrete pressure ranges P(x) requires changes to the pressure detection circuitry 250 shown in FIG. 5A, and one such alternative 250' is shown in FIG. 6A. As shown, n different comparators 252 receive the input signal Vin from the pressure sensor 77. Each comparator 252(x) receives a different reference voltage, Vref(x), and each generates a unique digital output 95, Pcrit(x). The different reference voltages are set using different values for resistors 91 and 94 (see FIG. 5A), and, in FIG. 6A, are made to decrease in subsequent comparators stages, with Vref1>Vref2, and so on. As the pressure increases, and as Vin decreases, each of the comparators 252(x) will set their digital outputs Pcrit(x) accordingly. No outputs are set (i.e., all Pcrit(x)='0') in the lowest pressure range P1, and the microcontroller 160 can set the maximum temperature for the external charger to its highest setting, Tmax1. As the pressure increases into range P2, only Pcrit1 is set, and the maximum temperature is set to a lower value of Tmax2. As the pressure increases further into range P3, both Pcrit1 and Pcrit2 are set, and the maximum temperature is set to an even lower value of Tmax3, etc. In this way, the n stages in the pressure detection circuitry allow for the detection of n+1 pressure ranges, which in turn allows for n+1 different maximum temperatures to be set. One skilled in the art will realize that pressure detection circuitry 250' is merely one way to detect a plurality of pressure ranges, and that other ways of indicating the presence of such ranges to the microcontroller 160 are possible.

In addition to, or in place of, adjusting the maximum temperature, the different sensed pressure regions P(x) can be used to control the external charger in different ways already mentioned. For example, entry into a higher pressure range can cause an alert to issue, or cause charging to be suspended, or cause some other modification to the temperature control scheme operable in the external charger to reduce its temperature, or combinations of these.

Figure 7A:
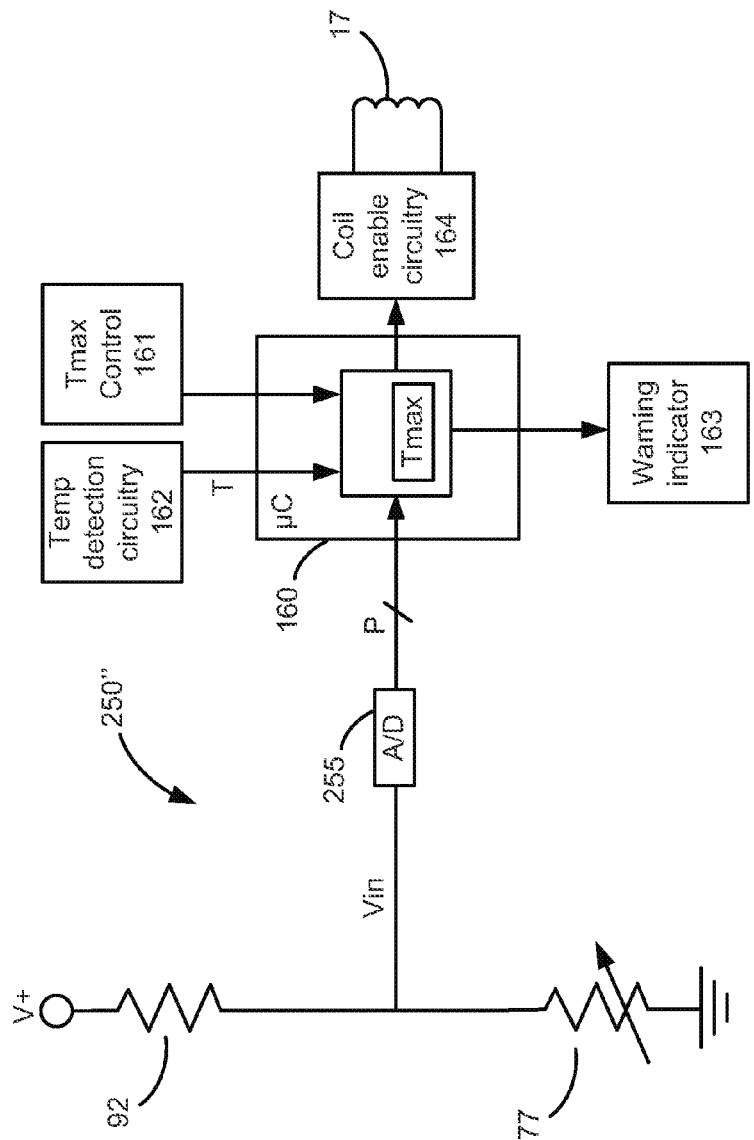
FIGS. 7A and 7B show control of the temperature of the external charger of FIG. 4 as a function of the sensed pressure in an analog fashion.
Figure 7B:
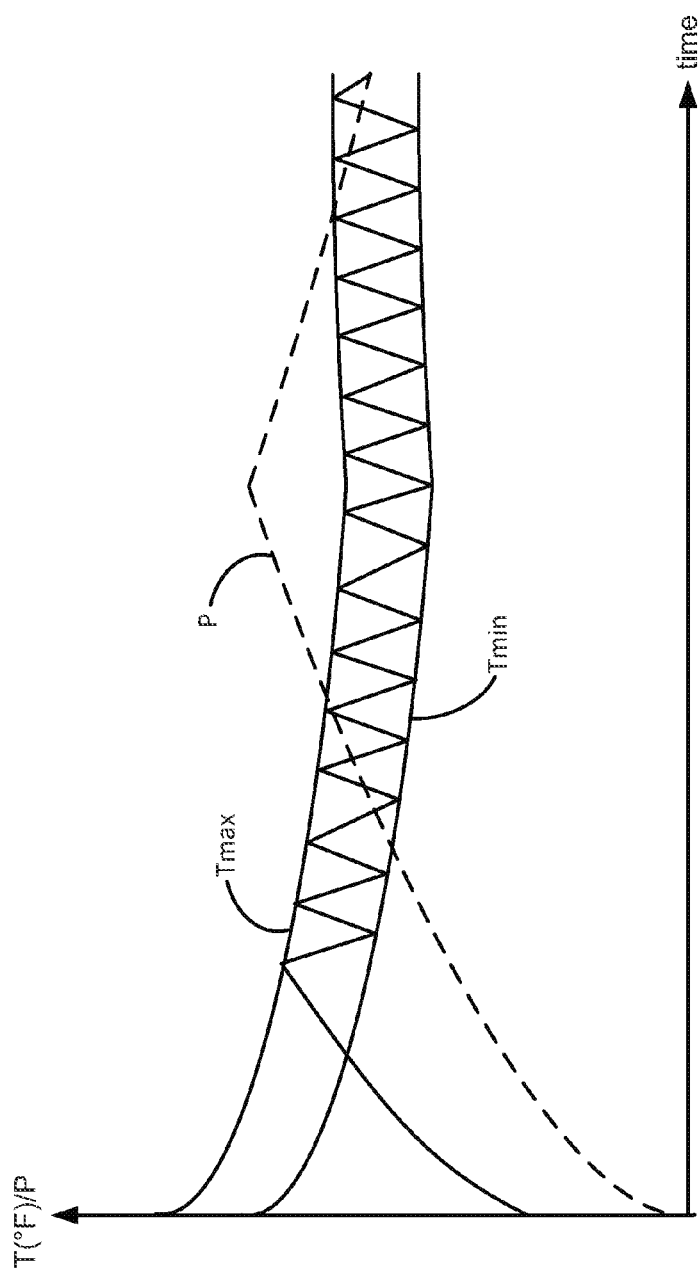

Control of the external charger 200 may also occur smoothly with the detected pressure in an analog fashion, as shown in FIGS. 7A and 7B. As shown in FIG. 7B, as the detected pressure P is increased, Tmax is likewise decreased in smooth fashion, and vice versa, without comparison to discrete pressure set points Pcrit(x) or pressure ranges P(x) as in earlier examples. One simple example of pressure detection circuitry 250" for achieving this result is shown in FIG. 7A, which merely uses an analog-to-digital converter 255 to digitize the analog input signal from the pressure sensor 77, Vin. Once received at the microcontroller 160, Tmax can then be adjusted smoothly as a function of the sensed pressure, P. Again, other circuitry configurations for providing analog control of the external charger 200 on the basis of the sensed pressure are possible, and pressure detection circuitry 250" is merely exemplary. And, as in earlier embodiments, control can also include alerts, suspension of charging, general modification of the external charger's temperature control scheme, etc.

Figure 8:
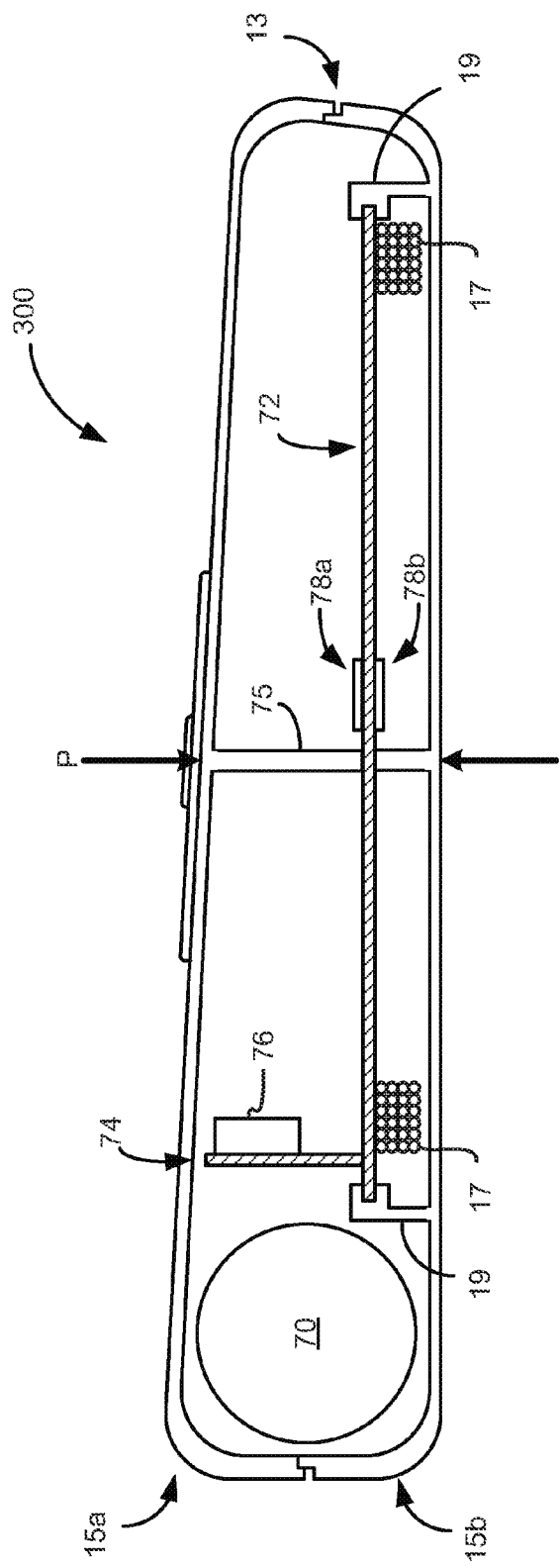
FIG. 8 shows an embodiment of an improved external charger, which includes a strain gauge and associated strain detection circuitry.

FIG. 8 shows another embodiment of an improved pressure-sensitive external charger 300. In this embodiment, the pressure sensors comprise strain gauges 78a and 78b. Strain gauges 78a and 78b may be mounted to PCB 72 or any other surface which will experience strain when external pressure P is applied to the charger 300. The strain gauges 78a and 78b may comprise, for example, part number KFRS-02-120-C1-13, manufactured by Kyowa Electronics Instrument Co. Ltd. As is well known, strain gauges change their resistance as they are stretched or compressed, and in the application of FIG. 8, the resistance of the strain gauges 78a and 78b will change as the PCB 72 bows in response to a pressure P that tends to warp or bend the case 15. As the surface of the PCB 72 bows, the strain gauge on the convex side will be under tension, which increases the resistance of the gauge, while the strain gauge on the concave side will be compressed, which decreases its resistance. Other strain gauges may behave differently, and no particular type of strain gauge is required. As before, one or more transfer elements 75a and 75b may be used to transfer forces from outside the case 15 to the PCB 72 and to the strain gauges 78a and 78b, but this is not strictly necessary depending on the physical design of the external charger at hand. Although two strain gauges are shown in FIG. 8, only one may be used, and may be located in other places inside or outside the case that experiences stress resulting from pressure on the case 15.

Figure 9:
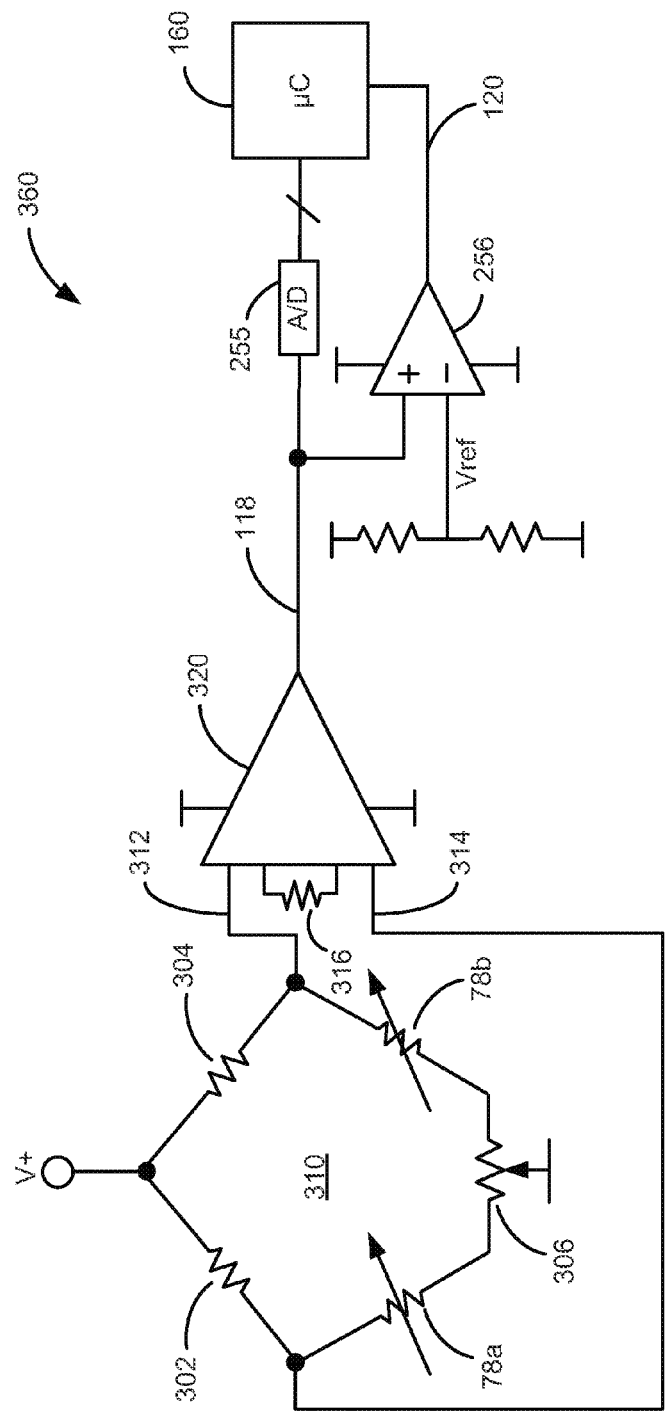
FIG. 9 shows a schematic of the strain gauge circuit of the external charger of FIG. 8.

By monitoring the resistances of the strain gauges 78a and 78b, the microcontroller 160 can determine the amount of strain on the PCB 72, and from this, infer the amount of external pressure on the external charger 300 and how its control should be modified as a result. FIG. 9 shows one embodiment of an example strain gauge circuit 360 usable in the improved external charger 300. In this embodiment, the strain gauge circuitry 360 comprises a bridge circuit 310 comprising resistors 302, 304, and 306, as well as the variable resistances provided by strain gauges 78a and 78b. Resistors 302 and 304 are used to balance the bridge circuit 310, and resistor 306 serves as a zero balance whose value can be adjusted to zero out the circuit when there is no strain present.

When pressure affects the strain gauges 78a and 78b, the voltage provided by inputs 312 and 314 will change inversely, thus providing inverse inputs to instrumentation amplifier 320. The difference in voltage of inputs 312 and 314 is amplified at the output 118 of the instrumentation amplifier 320. (A resistor 316 may be used to control the gain of the instrumentation amplifier 320).

Output 118 is thus indicative of the pressure, and can be used by the microcontroller 160 in various ways to modify the control scheme in any of the ways mentioned above. For example, if the microcontroller 160 will modify the temperature control scheme based on an analog value, such as occurred in FIGS. 7A and 7B, then the analog output 118 can be digitized by analog-to-digital converter 255 and provided to the microcontroller 160 for appropriate action: e.g., for Tmax adjustment, to alert the user, to suspend charging, to use a different or modified temperature control scheme for the external charger 300, or combinations of these. If, instead, the microcontroller 160 requires a digital input(s) indicative of critical pressure(s), output 118 can be compared to a reference voltage Vref at a comparator 256, similar to the techniques discussed above with reference to FIGS. 5A-6B. Assuming Vref is appropriately set, the comparator 256 of FIG. 9 will produce a digital output 120 indicating to the microcontroller 160 whether a critical pressure Pcrit has been exceeded, similar to the approach of FIGS. 5A and 5B. If additional comparators 256 are provided, each with unique reference voltages (not shown for convenience), the microcontroller 160 can be digitally informed of a ranges of pressures, similar to the approach of FIGS. 6A and 6B. Of course, depending on the approach chosen, either the comparator(s) 256 or the A-D converter 255 may not be required in an actual implementation of strain gauge circuitry 360. Again, strain gauge circuitry 360 is merely an example, and other circuitry capable of providing strain information can be used.

Figure 10:
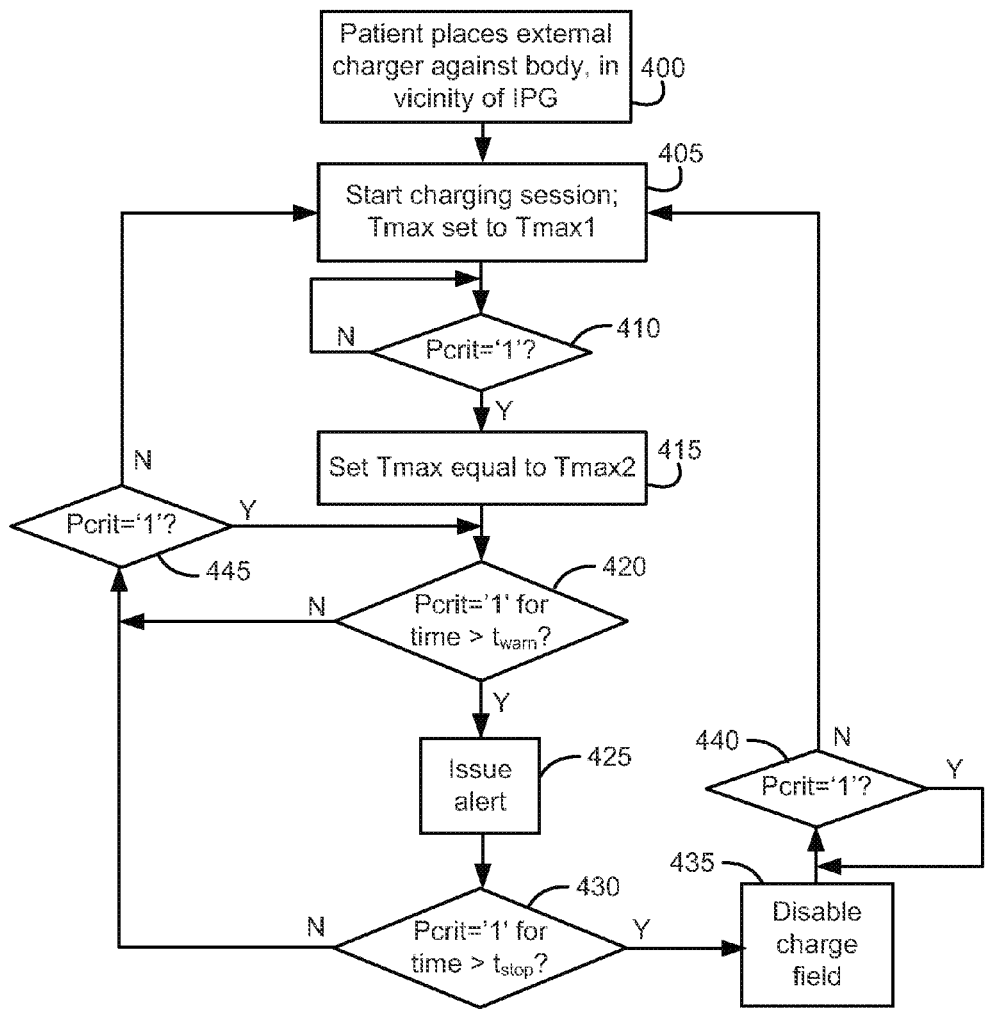
FIG. 10 shows a flow chart of one exemplary method for controlling an external charger as a function of external pressure.

FIG. 10 is a flow chart detailing one exemplary process for controlling charging based on the pressure impingent on the case of an external charger. In this example, control is based on whether a single critical pressure value, Pcrit, has been exceed, and so is similar to the example provided in FIGS. 5A and 5B discussed earlier. Either the pressure-sensor-based or strain-gauge-based detection circuits disclosed earlier can be used to make the critical pressure determination.

After the patient places the external charger against their body in the vicinity of the IPG 100 (Step 400), the patient can start a charging session using the user interface of the external charger (Step 405). At this point, the external charger may also set the maximum temperature to a relatively high maximum temperature set point value, Tmax1, and so may duty cycle the generation of the produced charging field to maintain that temperature as discussed earlier. During the charging session, microcontroller 160 continually monitors pressure levels in the case 15 of the external charger to determine whether the pressure is in excess of any critical pressure values, i.e., whether Pcrit='1' (Step 410). If the pressure level is not excessive, the external charger may continue to provide power to the IPG 100 as normal, and as subject to other traditional considerations such as the fullness of the IPG's battery 26. If, instead, the pressure level in the case 15 of the external charger is in excess of a critical level, i.e., Pcrit='1', microcontroller 160 may then set the maximum temperature to a new lower set point value, Tmax2, less likely to discomfort the patient (Step 415).

Next, microcontroller 160 determines whether the pressure level in the case 15 of the external charger has been in excess of the critical pressure value, Pcrit, for greater than a predetermined critical amount of time, $t_{warn}$, e.g., 15 minutes (Step 420). If not, the external charger may continue to provide power to the IPG 100 as normal, and can reset the maximum temperature set point back to the higher Tmax1 should the pressure later fall to below the critical level, i.e., if Pcrit='0' (Steps 445 and 405). If t is exceeded, the microcontroller 160 may issue an alert to the user in any of the abovementioned ways, such as any visual, auditory, or tactile feedback that is suitable for interpretation by the user of the external charger (Step 425).

After issuance of the alert, the microcontroller 160 can assess whether the pressure has been excessive for an even greater predetermined amount of time, $t_{stop}$, e.g., 30 minutes. If not, the external charger may continue to provide power to the IPG 100 as normal and can reset the maximum temperature set point back to the higher Tmax1 should the pressure later fall to below the critical level (Steps 445 and 405). If the pressure level in the case 15 has been excessive for greater than $t_{stop}$, the microcontroller 160 may suspend the wireless transmission of power during the charging session, e.g., by disabling the external charger's charge coil 17 (Step 435). The external charger may remain suspended until the pressure on the external charger decreases sufficiently that Pcrit is no longer set, i.e., Pcrit='0' (Step 440). Once this occurs, the charger may resume the wireless transmission of power during the charging session with Tmax set to Tmax1 (Step 405).

Because the external charger is often placed against a patient's back or buttocks, it can be difficult for the patient to receive alert information from the external charger. To provide better alert feedback to the patient, the external charger may optionally transmit alert information (See Step 425) via a suitable communications link to another external device, e.g., a remote control or external controller. Such additional external devices may then indicate any potentially unsafe conditions to the patient. This type of communication is disclosed in commonly-owned U.S. patent application Ser. No. 12/476,523, filed Jun. 2, 2009 ("the '523 application"). An alert may comprise the raw pressure data reported by the pressure detection circuitry, or a simple indication that pressure has exceeded the critical level and/or for how long.

Although it is envisioned that the disclosed external charger 200 would normally be used to charge or recharge a battery 26 within the IPG 100, the external charger 200 can also be used with IPGs or other implantable medical devices that lack a battery. This could occur for example in a system in which the IPG continually wirelessly receives energy from the external charger 200, which IPG in turn rectifies and uses this energy without storage.

Although a primary feature of this disclosure is the use of impingent pressure on the case to regulate the generated heat of the external charger, it should be noted that impingent pressure can be used to control the external charger in other more generic fashions. As already noted, sensed impingent pressure can be used to suspend charging or to issue a warning, which features are useful even if temperature control is not an issue. For example, it might be warranted to issue an alert or to suspend operation when high impingent pressures are present merely because such pressure may physically hurt the patient or damage the external charger.

Although discussed in the context of an external charger, it should be understood that detection of impingent case pressure can be used to control other sorts of devices in an implantable medical system. For example, impingent pressure can be used to similarly control an external controller which wirelessly transmits instructions used to program the implantable medical device or to wirelessly read status information therefrom, such as disclosed in used in the above-referenced '523 application.

Other types of pressure sensors may also be used in applications of the disclosed invention, such as ultrasonic transducers, carbon ink, and/or circuits employing such devices. Although this disclosure refers to "pressure" and the sensing of pressure, it should be understood that "pressure" includes "forces." "Pressure" should therefore be understood as inclusive of "force."

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external charger for an implantable medical device, comprising:
pressure detection circuitry configured to sense a pressure on the external charger;
temperature detection circuitry configured to sense a temperature; and control circuitry configured to transmit energy to the implantable medical device, wherein the control circuitry is further configured to maintain the sensed temperature in accordance with a temperature set point, wherein the sensed pressure is used to set the temperature set point.

2. The charger of claim 1, wherein the pressure detection circuitry compares the sensed pressure to a critical pressure value.

3. The charger of claim 2, wherein the critical pressure value is programmable.

4. The charger of claim 2, wherein the critical pressure value is set by a reference voltage in the pressure detection circuitry.

5. The charger of claim 2, wherein if the sensed pressure is below the critical pressure value, the temperature set point is set to a first temperature set point, and wherein if the sensed pressure exceeds the critical pressure value, the temperature set point is set to a second temperature set point.

6. The charger of claim 5, wherein the second temperature set point is lower than the first temperature set point.

7. The charger of claim 6, wherein the temperature set point is set to the second temperature set point if the sensed pressure exceeds the critical pressure value for a first amount of time.

8. The charger of claim 1, wherein the pressure detection circuitry converts the sensed pressure into one of a plurality of pressure ranges.

9. The charger of claim 8, wherein each of the plurality of pressure ranges is associated with a different temperature set point.

10. The charger of claim 9, wherein temperature set point associated with the one pressure range is used to set the temperature set point.

11. The charger of claim 1, wherein the temperature set point increases as the sensed pressure decreases, and wherein the temperature set point decreases as the sensed pressure increases.

12. The charger of claim 1, wherein the temperature set point comprises a maximum temperature set point.

13. The charger of claim 12, further comprising a minimum temperature set point, wherein the control circuitry is configured to maintain the sensed temperature between the maximum temperature set point and the minimum temperature set point.

14. The charger of claim 1, wherein the temperature detection circuitry comprises a thermocouple or a thermistor.

15. The charger of claim 1, wherein using the sensed pressure to set the temperature set point comprises selecting the temperature set point from a plurality of temperature set points.

16. The charger of claim 15, wherein the temperature set point values are programmable.

17. The charger of claim 1, wherein the control circuitry is configured to maintain the sensed temperature in accordance with the temperature set point by duty cycling the transmitted energy.

18. The charger of claim 1, further comprising a coil, wherein the control circuitry is configured to maintain the sensed temperature in accordance with the temperature set point by changing a current in the coil.

* * * * *